United States Patent [19]

Wideman

[11] 4,167,529
[45] Sep. 11, 1979

[54] SELECTIVE HYDROGENATION OF CYCLOPENTADIENE TO FORM CYCLOPENTENE USING RANEY NICKEL CATALYST AND AMMONIUM HYDROXIDE IN THE REACTION MIXTURE

[75] Inventor: Lawson G. Wideman, Akron, Ohio

[73] Assignee: The Goodyear Tire & Rubber Company, Akron, Ohio

[21] Appl. No.: 850,577

[22] Filed: Nov. 11, 1977

[51] Int. Cl.$^2$ .......................... C07C 5/06; C07C 5/16
[52] U.S. Cl. ................................................ 585/274
[58] Field of Search .................................. 260/666 A

[56] References Cited

U.S. PATENT DOCUMENTS

| | | | |
|---|---|---|---|
| 2,360,555 | 10/1944 | Evans | 260/666 A |
| 3,819,734 | 6/1974 | Kothari et al. | 260/666 A |
| 3,857,894 | 12/1974 | Morelli et al. | 260/666 A |

Primary Examiner—Veronica O'Keefe
Attorney, Agent, or Firm—J. Y. Clowney

[57] ABSTRACT

There is disclosed a process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel in which ammonium hydroxide is employed in the reaction mixture.

3 Claims, No Drawings

SELECTIVE HYDROGENATION OF CYCLOPENTADIENE TO FORM CYCLOPENTENE USING RANEY NICKEL CATALYST AND AMMONIUM HYDROXIDE IN THE REACTION MIXTURE

BACKGROUND OF THE INVENTION

This invention is directed to a selective hydrogenation of dienes to monoolefins, particularly of cyclopentadiene to cyclopentene. More specifically, it is directed to a process whereby cyclopentadiene is selectively hydrogenated to cyclopentene with the use of a highly dispersed form of nickel as a catalyst and ammonium hydroxide as a reaction medium.

At the present time, substantial amounts of cyclopentadiene, usually as dicyclopentadiene, are available as a byproduct from the steam cracking of naphtha, to produce primarily ethylene. Cyclopentene has been found to be useful as a monomer for the formation of general purpose elastomers by ring opening polymerization of cyclopentene. Therefore, it is desirable to convert a portion of the excess cyclopentadiene available into a more valuable raw material, such as cyclopentene.

The hydrogenation of cyclopentadiene to cyclopentene is not new. For instance, in U.S. Pat. No. 2,360,555, issued Oct. 17, 1944, there is disclosed a selective hydrogenation of one of the two conjugated double bonds of a cyclic diolefin to produce the corresponding cyclic monoolefin which is accomplished by conducting the hydrogenation in the liquid phase in the presence of an active hydrogenation catalyst, under moderate hydrogen pressure, such as 2 to 5 atmospheres absolute, and at relatively low temperatures, such as from 0° to 40° C. and even up to 100° C. using substantially less than the stoichiometric amount of hydrogen theoretically required to completely reduce the cyclic diene to the corresponding cyclic monoolefin. The catalyst therein disclosed is a pyrophoric nickel metal catalyst, such as Raney nickel. It is also disclosed that it is desired to conduct the reaction in dilute solution. The dilution may be affected by the addition of any solvent, stable under conditions of the process and which is not a catalyst poison and whose boiling point is such as to render it easily separable from the reaction mixture. Benzene and ethanol as well as tetralin, dioxane, isooctane, ethyl ether and diisopropyl ether are disclosed as such solvents in such process.

In U.S. Pat. No. 3,819,734, issued July 25, 1974, there is disclosed the hydrogenation of cyclopentadiene to cyclopentene by bringing cyclopentadiene into contact with a catalyst consisting essentially of (1) nickel, on a magnesium or zinc oxalate support, (2) a ligand selected from the group consisting of trimethyl phosphine, triethyl phosphine, methyl ethyl propyl phosphine, trimethyl phosphite, triethyl phosphite, tributyl phosphite, triphenyl phosphite, etc., while in the presence of hydrogen, at temperatures from 0° C., and at pressures from 0 to 1000 pounds per square inch gauge. The solvent mentioned therein is ethanol.

In U.S. Pat. No. 3,994,986, issued Nov. 30, 1976, there is disclosed the preparation of cyclopentene from cyclopentadiene by hydrogenating cyclopentene with hydrogen gas at a ratio of 1 to 1.5 moles of hydrogen per mole of cyclopentadiene in the presence of a palladium catalyst on a carrier.

Also, in U.S. Pat. No. 3,857,894, issued Dec. 31, 1974, there is disclosed the hydrogenation of cyclopentadiene to cyclopentene in the presence of a palladium catalyst and a small amount of an aqueous solution of zinc salt having a water/zinc ratio of at least 1/1 by weight. There is also mentioned that an amine, such as ammonia, may also be present in an amount of not more than 0.5 weight percent of the cyclopentadiene.

The cyclopentadiene employed in the formation of cyclopentene by hydrogenation is usually obtained by depolymerizing or cracking dicyclopentadiene. In order to obtain cyclopentadiene for the hydrogenation of this invention, the depolymerization of dicyclopentadiene is accomplished by heating the dimer at a temperature above 150° C., under atmospheric pressure in a conventional cracking apparatus. The depolymerized material should be hydrogenated without substantial delay because it is also known that redimerization will occur upon standing.

SUMMARY OF THE INVENTION

According to the invention, cyclopentadiene can be selectively hydrogenated to cyclopentene in the liquid phase by contacting cyclopentadiene with hydrogen in the presence of a catalyst comprising a highly dispersed form of nickel and in which ammonium hydroxide is employed in the reaction mixture.

It has been found that in order to have a fairly selectively hydrogenation for cyclopentene, a reaction medium or a diluent must be employed. According to the present invention, ammonium hydroxide is employed as a reaction medium.

Certain advantages are inherent in the use of ammonium hydroxide as a reactive medium. The presence of ammonium hydroxide aids greatly in moderating the exothermic nature of the hydrogenation of cyclopentadiene. The use of ammonium hydroxide as a reaction medium is a further advantage in that further hydrogenation of the cyclopentene to cyclopentane does not appear to take place in any appreciable extent when all of the cyclopentadiene has been consumed. Ammonium hydroxide seems to exhibit an inhibiting effect on the hydrogenation of cyclopentene in the presence of Raney nickel catalyst and hydrogen. Further, since cyclopentadiene and cyclopentene are not soluble in the ammonium hydroxide, the use of an ammonium hydroxide as the reaction medium in the hydrogenation of this invention causes the process to be a two-phase system. Because of this two-phase system, there is provided a method of separation of the reaction medium and the product cyclopentene and the unreacted cyclopentadiene. Still another advantage in using ammonium hydroxide as the reaction medium allows the cyclopentadiene feedstock, which has been formed by the steam cracking of dicyclopentadiene, to be employed in an undried form.

DETAILED DESCRIPTION OF THE INVENTION

The temperature at which cyclopentadiene may be hydrogenated in accordance with this invention may range from 0° to 75° C. with 20° to 30° C. being most preferred. Temperatures that approach 100° C. tend to consume the cyclopentadiene in side reactions, such as dimerizations back to dicyclopentadiene and other undesirable side reactions. Generally speaking, both temperature and the pressure of hydrogen employed should be kept as low as possible consistent with reasonable rates of hydrogenation. When faster rates of reaction than that being obtained is desired, it is preferable to increase the rate of hydrogenation by means of increased hydrogen pressure rather than an increase in the temperature.

High hydrogen pressures may be employed to effect faster rates of hydrogenation, however, it has been found in accordance with the present invention that about 150 psig—1035.5 kPa is all that is required to give a reasonable rate of reaction.

The reaction medium, ammonium hydroxide, is not conducive to the solubility of the cyclopentadiene and thereby renders the process a two-phase system that requires some vigorous agitation. Upon agitation, the ammonium hydroxide serves as a heat sink by absorbing unwanted heat from the reaction site and, hence, moderates the hydrogenation, thereby enhancing the selectivity for the cyclopentene.

The presence of a two-phase system when the agitation is stopped also offers the advantage that the catalyst settles to the bottom of the lower ammonium hydroxide layer and the organic phase at the top, thus, they are separated with ease. Ammonium hydroxide also serves to protect the catalyst from air and thereby facilitates an easy recycling of the catalyst.

The catalyst employed in the present invention is a highly dispersed form of nickel. However, a Raney nickel-type catalyst is preferred. Methods for preparing the Raney nickel catalyst which are useful in this invention are known and can be found in a book entitled "CATALYTIC HYDROGENATION", by Robert L. Augstine, published in 1965 by Marcel Dekker, Inc., New York, N.Y.

Temperatures employed to prepare Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred, or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry, 7, 586, (1942) and Papa, Schwenk and Brieger in the Journal of Organic Chemistry, 14, 366, (1949). All of the Raney nickels described in the articles referred to above are operable in the process of this invention.

Other nickel catalysts useful in the invention can be obtained by the use of new techniques known to the catalyst art for depositing metals on suitable supports in a highly dipsersed form. These nickel catalysts would exhibit catalytic properties similar to the properties exhibited by the Raney nickel catalysts.

In the article by Dominguez et al, the authors state that the T-1 Raney nickel is prepared as follows:

To a 1-liter 3-neck flask containing 600 ml of a 10 percent sodium hydroxide solution, 40 grams of Raney nickel aluminum alloy (50 percent nickel) were added in small portions over a period of 20 to 30 minutes with mechanical stirring. The temperature was kept at 90°–95° C. during this addition. The mixture was stirred for an additional hour period at which time the stirring was stopped and the nickel was allowed to settle, and the solution decanted. The metal was washed 5 times with 200-ml portions of water and then 5 times with 50-ml portions of ethanol in such a manner that the nickel was always covered with liquid. The catalyst was then stored under ethanol and refrigerated for further use.

The Raney nickel employed in some of the examples of this invention, and termed by the present inventor as Modified T-1 Raney nickel, was prepared by a slight modification of Dominguez et al's procedure and is as follows:

A solution of 2 grams of sodium hydroxide in 50 ml of water was heated to its boiling point and then there was added 2 grams of Raney nickel aluminum alloy (1 gram of Raney nickel) as rapidly as the hydrogen evolution would permit. This mixture was then digested at 95° to 100° C. for ¼ hour (reflux) and the water was continually replaced as it evaporated. The solution was decanted from the Raney nickel and the metal washed with three 250-ml portions of cold water. This catalyst was employed without washing with ethanol.

The ratio of catalyst to cyclopentadiene is not too critical. It has been found satisfactory results are obtained when about 1 part by weight of catalyst per 500 parts by weight of cyclopentadiene are employed. When a catalyst to cyclopentadiene weight ratio greater than about 1 to 33 is employed, the catalyst is being wasted.

The amount of ammonium hydroxide employed should range from about a volume ratio of ammonium hydroxide to cyclopentadiene of about 1/1 to about 4/1.

The ammonium hydroxide solution which is employed as the reaction medium is commercial grade which contains about 30 percent ammonia by weight.

The present invention can be applied to continuous or batch processes. While the ratios of catalyst to cyclopentadiene set forth is more applicable to batch processing, those skilled in the art could readily adapt the reactants, catalyst and reaction conditions to continuous processing.

The practice of this invention is further illustrated by reference to the following examples which are intended to be representative rather than restrictive of the scope of the invention. Unless otherwise indicated, all parts and percentages are by weight.

EXAMPLE 1

A one-liter stainless steel reactor was swept with nitrogen and charged with 100 milliliters (ml) of a 30 percent ammonium hydroxide, and one gram of a modified T-1 Raney nickel. Next, 66 grams of cyclopentadiene containing 0.5 gram of pentane as an internal chromatographic standard was then added under nitrogen. The reactor was sealed and charged with hydrogen to 150 psig—1035.5 kPa with stirring. The temperature was held at 25°–30° C. by means of internal cooling coils. The calculated one molar equivalent of hydrogen was consumed after 20 minutes. The hydrogen pressure was held almost constant for another 20 minutes. The agitation was stopped and the catalyst settled out in the ammonium hydroxide phase. The organic phase and the ammonium hydroxide phase separated within a few seconds—the top layer, the organic phase was drawn out of the reactor via an adjustable dip-leg and diluted with secondary butanol for gas chromatographic analysis. The analysis revealed 100% conversion of the cyclopentadiene and a 99.3% selectivity to cyclopentene and a 0.6% selectivity to cyclopentane.

EXAMPLE 2

A series of experiments were conducted in a manner similar to that of Example 1. In all of the experiments, 66 grams of cyclopentadiene were charged. In all of the experiments, one gram of modified T-1 Raney nickel catalyst was employed except Experiment 8 in which 0.5 gram was employed. In certain of the experiments, varying amounts of 30 percent ammonium hydroxide were employed. In other experiments, the 30 percent ammonium hydroxide was further diluted with additional water. These are noted in the table below. Other operating conditions and the results are set forth in the table below.

TABLE

| Exp No | Water (ml) | NH4OH (ml) | Rx Time (min) | H2 Pres (psig) | Conv CPD (%) | Sel CPE (%) | Sel CPA (%) |
|---|---|---|---|---|---|---|---|
| 1 | 300 | 1 | 90 | 100-150 | 89.3 | 89.6 | 7.8 |
| 2 | 250 | 50 | 58 | 100-150 | 95.6 | 96.2 | 3.8 |
| 3 | 200 | 100 | 66 | 100-150 | 92.7 | 98.9 | 1.2 |
| 4 | 100 | 200 | 80 | 100-150 | 91.9 | 99.6 | 0.3 |
| 5 | 0 | 200 | 80 | 100-150 | 100 | 99.6 | 0.3 |
| 6 | 0 | 100 | 39 | 250-300 | 98.7 | 99.5 | 0.6 |
| 7 | 0 | 100 | 35 | 350-400 | 99.6 | 99.0 | 1.1 |
| 8 | 0 | 100 | 70 | 250-300 | 98.4 | 98.5 | 1.6 |
| 9 | 0 | 300 | 55 | 250-300 | 98.8 | 98.9 | 1.2 |

While certain representative embodiments and details have been shown for the purpose of illustrating the invention, it will be apparent to those skilled in this art that various changes and modifications may be made therein without departing from the spirit or scope of the invention.

What is claimed is:

1. The process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel selected from the group consisting of Ranel nickel or modified Ranel nickel in which ammonium hydroxide is employed in the reaction mixture in the volume ratio of ammonium hydroxide to cyclopentadiene of from 1/1 to 4/1.

2. A process according to claim 1 in which the temperature ranges from 20° to 30° C.

3. The process according to claim 1 in which the pressure of the hydrogen is at least 150 psig—1035.5 kPa.